United States Patent [19]
Kawazoe et al.

[11] 4,266,196
[45] May 5, 1981

[54] GAS DETECTING MEANS UTILIZING ELECTRIC DISCHARGE

[75] Inventors: Kazuyoshi Kawazoe, Takahagi; Yoshinori Takata, Ibaraki; Mon Suzuki, Hitachi; Shizuo Uehara, Ibaraki, all of Japan

[73] Assignee: Hitachi, Ltd., Tokyo, Japan

[21] Appl. No.: 25,571

[22] Filed: Mar. 30, 1979

[30] Foreign Application Priority Data

Mar. 31, 1978 [JP] Japan .................... 53/36614

[51] Int. Cl.³ .................................. G01N 27/62
[52] U.S. Cl. ............................ 324/464; 313/231.7; 315/111.9
[58] Field of Search ............. 313/231.7; 315/111.9, 315/111.8; 324/464; 250/423 P, 382

[56] References Cited
U.S. PATENT DOCUMENTS

| 1,564,694 | 12/1925 | Lerchen | 313/313 X |
| 1,958,953 | 5/1934 | Parker | 313/313 X |
| 3,379,968 | 4/1968 | Yamane | 324/464 |
| 3,418,514 | 12/1968 | Sternberg | 313/231.7 |
| 3,454,828 | 7/1979 | Yamane | 315/111.9 |
| 4,028,617 | 6/1977 | Kamo et al. | 324/464 |

Primary Examiner—Alfred E. Smith
Assistant Examiner—Thomas P. O'Hare
Attorney, Agent, or Firm—Craig and Antonelli

[57] ABSTRACT

A gas detecting means of this invention is provided with a discharge section which radiates light by electric discharge, a detecting section which collects an ion current of a sample gas ionized by the light, and an optical path which connects the discharge and the detecting sections. The discharge is formed by a pointed cathode and an anode having a penetration hole. The tip of the pointed cathode is directed to the optical path. The diameter of the penetration hole of the anode is smaller than that of the optical path. The anode is disposed in such a manner that any peripheral part of an inlet of the penetration hole is at an equal distance from the tip of the cathode. Both the discharge section and the detecting section are shielded electrically by an outer shell of metal.

27 Claims, 8 Drawing Figures

GAS DETECTING MEANS UTILIZING ELECTRIC DISCHARGE

BACKGROUND OF THE INVENTION

The invention relates to a means for detecting gas, in which the light generated by discharge phenomena is radiated to a gaseous sample to ionize it and ions thereby generated are electrically detected. The photoionization detector is constructed in such a manner that ultraviolet light is generated by a discharge in the presence of a discharge gas; the light is guided into a detecting section to photoionize the sample gas; the sample gas ions are collected by a collector electrode in the detection section to measure the ionization current. Since a photoionization detector has excellent characteristics such as a high sensitivity of detection and a capability of detecting both inorganic and organic constituents, it is suited to a detector for gas chromatography.

As a prior art related to this invention, U.S. Pat. No. 4,028,617 is known. A means according to this patent comprises a discharge section which radiates light of electric discharge, a detecting section which collects an ion current generated by photoionization of a sample gas, and a light path which communicates the discharge section and the detecting section. A cathode for discharge has a tip directed to the light path. An anode for discharge forms a wall of the light path. Compared to a means known prior to the above U.S. patent, in which two bar electrodes are placed in a discharge chamber to obtain a spark discharge, the stability of discharge is improved and the base line variation was reduced to an order of $2 \times 10^{-12}$ A. However, this value does not yet reach a value of variation $2 \times 10^{-13}$ A, which is necessary for a practical use of a detector of this type.

SUMMARY OF THE INVENTION

One object of this invention is to provide a gas detecting means using discharge and capable of obtaining a measuring accuracy high enough for practical use.

Another object of this invention is to provide a gas detection means which maintains a stable discharge in the discharge section.

A further object of this invention is to provide a gas detection means free from any externally induced noise.

According to this invention, a communicating path is provided to pass light from a first chamber, or a discharge section, into a second chamber, or a detecting section. A pointed discharge electrode is directed to the communicating path. A discharge counter electrode is provided between the pointed discharge electrode and the second chamber. This discharge counter electrode has a penetration hole with a size smaller than the spatial cross-section of the communicating path. The discharge counter electrode is so arranged that the penetration hole becomes an inlet of the light which passes through the communicating path.

According to a preferred embodiment of this invention, the wall of the communicating path is formed by an electric insulator and the discharge counter electrode is disposed in such a manner that any part of the periphery of the penetration hole is substantially at an equal distance from the tip of the pointed discharge electrode.

According another preferred embodiment of this invention, the walls of first and second chambers are formed by an electric insulator, and the outer surface of the electrically insulating wall is covered with metal to shield it electrically and thereby to eliminate externally induced noise.

DESCRIPTION OF THE PREFERRED EMBODIMENTS

Figure 1:
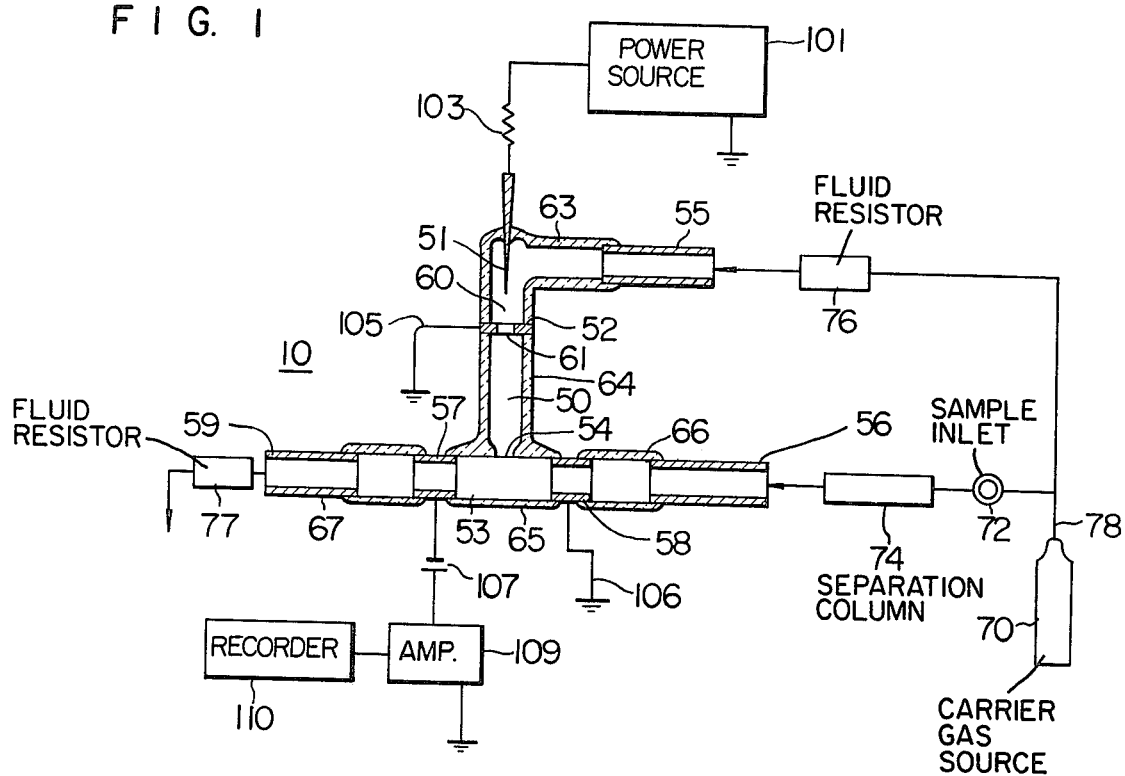
FIG. 1 is a cross-sectional view of the main part showing a rough construction of one embodiment of this invention.

In FIG. 1 showing a cross-sectional view of the main part of a rough construction of one embodiment of this invention, a gas detecting means 10 comprises a first chamber 60 which is a discharge section for radiating ultraviolet light, a second chamber 53 which is a detection section for collecting an ion current of the sample gas ionized by the light, and a light path which communicates the both sections. A pointed discharge electrode 51 in the discharge section 60 is directed to the communicating path 50. A discharge counter electrode 52 disposed perpendicularly to the optical axis is placed between the tip of the pointed electrode or cathode 51 and a second chamber 53.

A flow path 78 connected to a carrier gas source 70 is branched, the one branch being connected to a discharge gas flow inlet 55 through a fluid resistor 76 while the other branch being connected to a sample gas inlet 56 through a sample inlet 72 and a separation column 74. The cathode 51 is connected to a power source 101 through an electric resistor 103. The anode 52 is grounded through a lead wire 105. A circular cylindrical electrode 57 in the detecting section 53 is connected to a recorder 110 through a battery 107 and an amplifier 109. A circular cylindrical collector counter electrode 58 is grounded through a lead wire 106.

The discharge counter electrode 52 is made of a planar metal and has a penetration hole 61 in the central portion thereof. The size of the hole 61 is smaller than the spatial cross-section of the communicating path 50. Namely, the discharge counter electrode 52 projects toward the light path so that the perforation hole 61 becomes an inlet of light into the communicating path 50. In this embodiment, the shape of the cross-section of the part projecting into the space of the discharge counter electrode 52 is rectangular.

A discharge gas introduced from the discharge gas inlet 55 is exhausted through the discharge section 60, the detecting section 53, the gas outlet 59 and the fluid resistor 77. The carrier gas for carrying a sample which is introduced from the sample gas inlet 56 is exhausted from the gas outlet 59 through the detecting section 53. The light generated in the discharge section 60 reaches the detecting section via the light passage hole 61. The wall 63 of the discharge section 60, the wall 64 of the communicating path 64 and the walls 65, 66 and 67 of the detecting section 53 are made of an electric insulator such as glass and ceramic.

Figure 2:
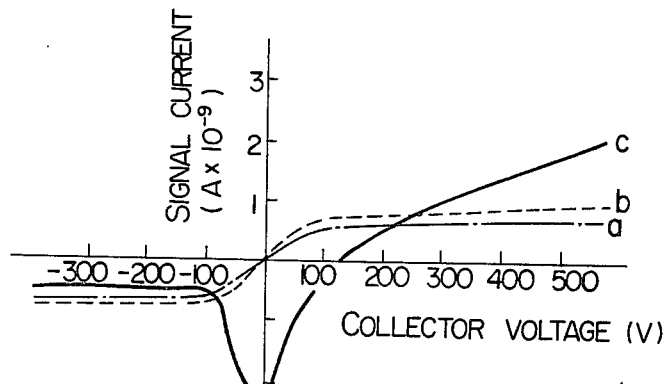
FIG. 2 is a diagram for the explanation of the voltage-current characteristic.

The detection means of FIG. 1 exhibits a characteristic as shown by a curve C of FIG. 2 when a nozzle portion 54 is not provided. That is, the signal current varies with a change of collector voltage. This phenomenon arises from an influence of electric fields of the discharge electrode 51 and the discharge counter electrode 52. In order to avoid this, a necessary structure is that a nozzle 54 is provided between the discharge counter electrode or the grounded pole 52 and the detecting section 53 to increase the speed of flow of the discharge gas streaming into the detecting section 53 and reduce the influence of ions and electrons generated by the photoionization of a sample to be detected.

Figure 3:
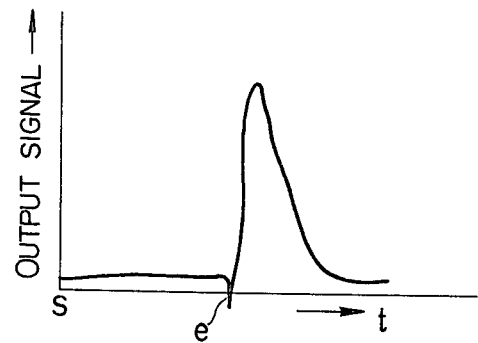
FIG. 3 is a diagram for the explanation of a signal peak of a detector shown in FIG. 1.

However, it is difficult in FIG. 1 to remove the influence of the discharge electrode 51 and the discharge counter electrode 52 completely. If the detecting means shown in FIG. 1 is applied to gas chromatography, a peculiar phenomenon is obtained in a signal peak of the sample flowing out of a separation column attached to the gas chromatograph, as shown in FIG. 3. That is, a singular point e appears before the peak.

If a nozzle 54 is provided at the detecting section, the detection sensitivity decreases due to a loss of light energy. If the discharge current is increased in order to enhance the light energy, sputtering of the discharge electrodes becomes considerably large, causing a reduction in the life of the detector.

The inventors have made an experiment with the embodiment of FIG. 1 by using a planar electrode as the discharge counter electrode 52 and placing it opposite to the pointed discharge electrode, and succeeded in improving the stability of discharge and reducing the noise level to about $2 \times 10^{-13}$ A. Without being satisfied with the result, the inventors have made an effort in making a detector free from such a problem as encountered in the detector of FIG. 1. Explanation of a detecting means as a result of the investigation will be made hereinafter.

Figure 4:
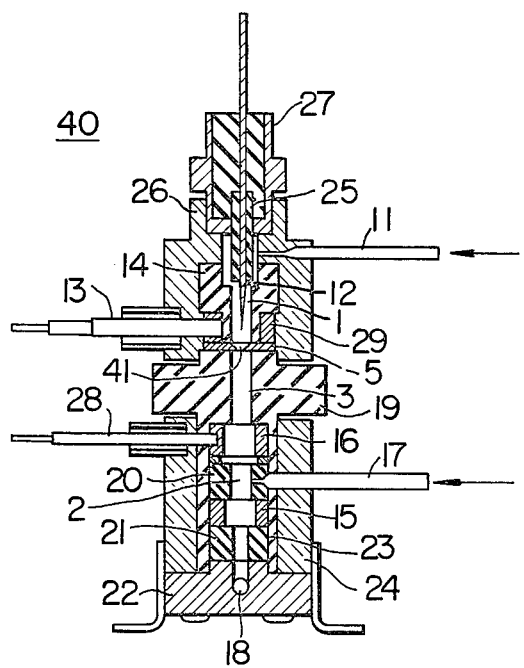
FIG. 4 is a cross-sectional view of the main part showing a rough construction of another embodiment of this invention.
Figure 5:
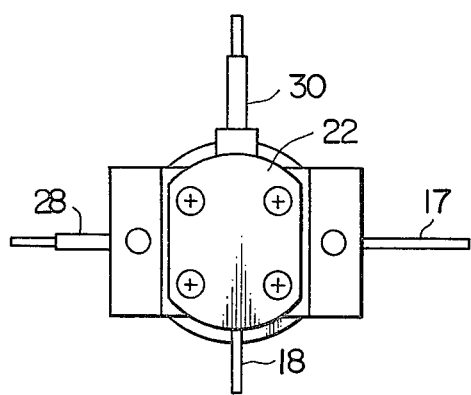
FIG. 5 is a bottom view of the embodiment of FIG. 4.
Figure 7:
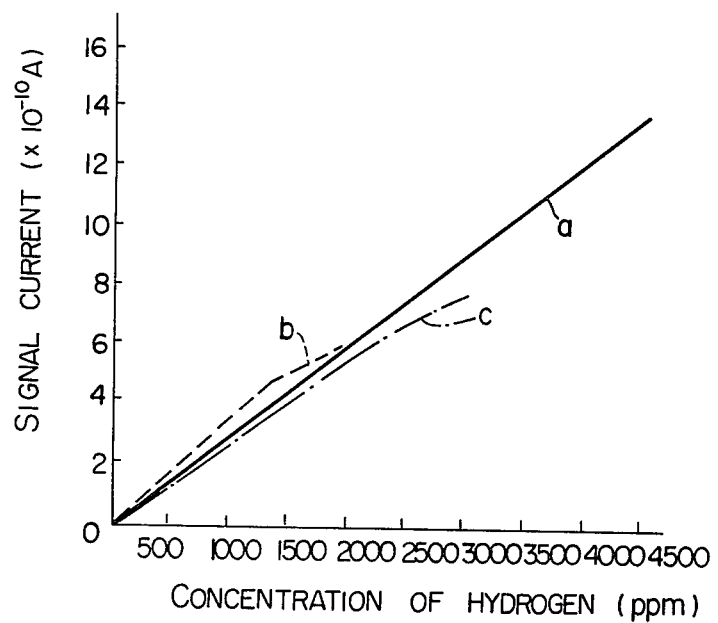
FIG. 7 is a diagram showing detected values of hydrogen gas obtained in each embodiment of FIG. 1, FIG. 4 and FIG. 6.

FIGS. 4 and 5 are drawings for the explanation of other embodiments of this invention. In a detecting means 40 of the embodiment, a discharge chamber 1 is formed by substantially a circular cylindrical electric insulator 14, an electric insulator 25 for supporting a pointed discharge electrode 12 and a fixing metal member 26. The electrode 12 is connected to a power source similarly to that of the example of FIG. 1. A detecting chamber 2 is formed by circular cylindrical electric insulators 20 and 21, a circular cylindrical collector electrode 15 and a circular cylindrical collector counter electrode 16. A communicating path 3 is formed by a circular cylindrical electric insulator 19. Between the insulators 14 and 19, a discharge counter electrode (grounded electrode) 5 is inserted in such a manner as to oppose to the discharge electrode 12. The discharge counter electrode 5 is provided with a conical penetration hole 41. The smaller inner diameter of the penetration hole 41 is smaller than the diameter of the path 3 of the electric insulator 19. Namely, the inner surface of the discharge counter electrode 5 projects toward the center to narrow the whole periphery thereof. Any part of the periphery of the penetration hole 41 is substantially at equal distance from the tip of the cathode 12. Insulators 14, 19, 20, 21, 23 and 25 are made of alumina or silica. A cap 27 for supporting the cathode 12 is fixed to a metal member 26.

The discharge gas is introduced into the discharge chamber 1 through an inlet pipe 11. When discharge occurs in the discharge chamber 1, the field lines of the electric field applied to the discharge electrode concentrate toward the tip of the pointed cathode 12. Since the discharge position does not fluctuate on the circular periphery of the hole 41 of the anode 5, a stable glow discharge is obtained. Furthermore, since the side wall of the discharge chamber is covered with insulating material, the space charge is not inclined by discharge so that discharge does not occur outside the electrodes, promoting thus the stability of discharge. The discharge counter electrode 5 makes contact with a metal ring 29 and the metal member 26, which are disposed around the outer periphery of the insulator 14, and is connected electrically to a ground terminal 13 through these members.

An inlet pipe 17 for introducing the sample gas opens between the collector electrode 15 and the collector counter electrode 16 in the detecting chamber 2. The discharge gas and the sample gas are exhausted from an outlet 18 after passing through the detecting chamber 2. The collector electrode 15 is constructed with a metal cylinder whose inner diameter is made larger than those of the circular cylindrical insulators 19, 20, and 21 in order not to generate any secondary electron due to radiation of light on the collector electrode. The collector counter electrode 16 is constructed similarly and, together with the collector electrode, is fixed to a circular cylindrical insulator 23 of alumina through packing material with a large malleability. To ensure an air-tight property without leakage of gas, they are also fixed to a fixing metal member 22. The outer side of the circular cylindrical insulator 23 is surrounded with a circular cylindrical metal member 24. The ground terminal 28 makes contact with the collector counter electrode 16 and the metal member 24 for electric connection.

The shape of the cross-section of a part projecting into the space in the discharge counter electrode 5 is a wedge directing toward the center of the penetration hole 41. The light generated by discharge is radiated into the detecting chamber 2 through the penetration hole 41. The sample gas introduced from the inlet pipe 17 flows to the gas outlet 18 in parallel with the light path. The introduced sample gas is ionized by light, and the ionization current is collected by the collector electrode 15 and monitored by a recorder which is similar to the one in FIG. 1. The numeral 30 denotes a signal terminal connected electrically to the collector electrode 15.

The arrangement, in which the discharge counter electrode 5 is made planar; the light passage hole is made to be a circular slit with a function of forming an optical path; and the planar surface and the pointed discharge electrode 12 are disposed perpendicularly to each other; removed substantially any movement of discharge point and maintained a stable discharge. Furthermore, by a series disposition of the collector electrode 15 and the collector counter electrode 16 along the optical path, the signal characteristic was improved.

Since the wall surfaces of the discharge chamber and the detecting chamber are made of an insulator, these chambers have a high impedance. In such a case, the detected signal is influenced by externally induced noise. In the example of FIG. 4, the outer sides of the discharge chamber and the detecting chamber are electrically shielded by conductive metal members 22, 24 and 26, which serve also as a support for the insulating members 14, 21 and 23. A prior art photoionization detector, which was constructed with glass except at the electrode parts, had a difficulty in the elimination of noise from the detected signal.

According to the embodiment of FIG. 4, the value of variation in the base line (including a drift in 30 minutes) and the noise level were reduced to $1 \times 10^{-13}$ A and $0.3 \times 10^{-13}$ A respectively. As a result, practical use of the detector for gas chromatography, in which a measurement of a very small quantity is required, became possible.

Figure 6:
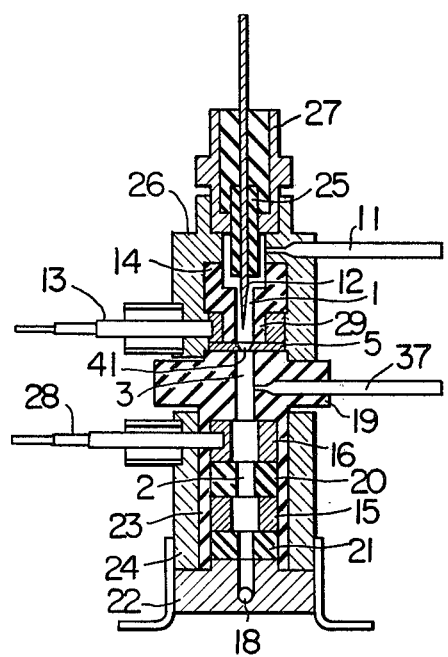
FIG. 6 is a cross-sectional view of the main part showing a rough construction of a further embodiment of this invention.

FIG. 6 shows a rough construction view of a further embodiment of this invention. All the parts other than the position of the inlet pipe for introducing the sample gas are the same as those of the embodiment in FIG. 4, so that a similar effect is obtained as in FIG. 4. Like reference numerals are used to denote like parts with the same function as that in FIG. 4.

FIG. 2 shows a relationship between the collector voltage and the signal current as obtained by the detecting means of FIGS. 1, 4 and 6. A curve a represents the characteristic of the means of FIG. 4, while a curve b represents that of the means of FIG. 6. The curve c corresponds to a case of removing the nozzle 54 from the embodiment of FIG. 1. It is understood that the signal currents exhibited by curves a and b varies little with the collector voltage so that a stable measured value is obtained.

Figure 8:
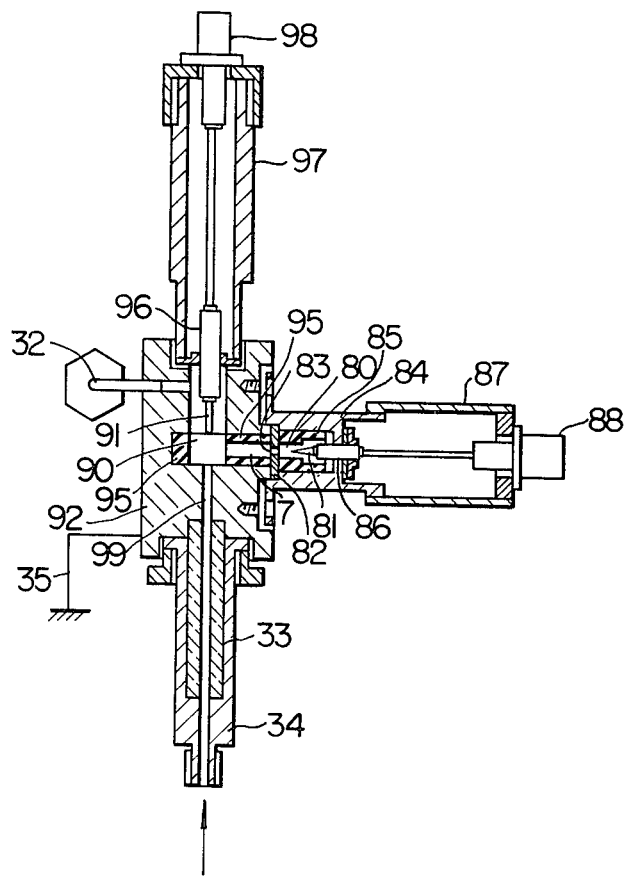
FIG. 8 is a cross-sectional view of the main part showing another embodiment of this invention.

FIG. 8 is a cross-sectional view showing a rough construction of another embodiment of this invention. A discharge chamber 80 is formed by a circular cylindrical electric insulator 85 with a step, an electric insulator 86 covering a pointed discharge electrode 81, and a metal member 84 protecting the insulator 85. The pointed electrode 81 is connected to a power source terminal 88, which is fixed to a cover 87. A detecting chamber 90 is formed by an electric insulator 95 having two perpendicular paths, and a metal member 92 having a sample introduction path 99. The metal member 92 is provided with a gas exhausting outlet connected to a gas outlet pipe 32. A collector electrode 91 inserted in the detecting chamber 90 is connected to a signal terminal 98. An electric insulator 96 covers the collector electrode 91. The signal terminal 98 is fixed to a cover 97. A capillary tube 33 is fixed by a supporting member 34 to be guided to the sample introduction path 99. A communicating path 7 is formed in the electric insulator 95. A disk-like discharge counter electrode 82 is inserted between the electric insulators 85 and 95. A circular penetration hole 83 is formed in the counter electrode 82. The diameter of the hole 83 is smaller than those of the communicating path 7 and the insulator 85. The pointed electrode 81 is directed to the center of the penetration hole 83.

The sample gas is made to flow through the capillary tube 33 toward the collector electrode 91. The light generated by discharge in the discharge chamber 80 is radiated to the sample gas in the detecting chamber 90 with its optical path limited by the penetration hole 83 of the anode 82.

The discharge counter electrode is formed by the metal member 92 and grounded through a lead wire 35. The metal member 92 covers the outer surface of the electric insulator 95. Namely, the metal member 92 has functions of serving as a collector counter electrode and also as a means for shielding externally induced noise from the detecting section 90. The metal member 84 has a function as a means for electrically shielding the discharge section 80. Since the discharge counter electrode 82 is made contact with the metal members 84 and 92, it is effectively grounded.

In the detecting means in the above-mentioned embodiments, discharge occurs under the condition of atmospheric pressure, using an inert gas as the discharge gas. In this case, characteristic light is generated depending on the kind of discharge gas. For example, if helium is used as the discharge gas, light with a wavelength of about 600 A is generated, the work function of which is about 21 eV. Since the ionization potentials of oxygen and nitrogen are 12.2 eV and 15.5 eV respectively, these gases are ionized by the light from the discharge section when they are introduced as sample gases. As a result, an ion current due to ionization can be detected, giving an output signal.

We claim:

1. A gas ionization detector comprising,
   a first chamber;
   a second chamber;
   means forming a communicating path between said first and second chambers to guide light from said first chamber into said second chamber;
   a pointed discharge electrode placed in said first chamber and directed toward said communicating path;
   a discharge counter electrode having a penetration hole with a diameter smaller than the spatial cross-section of said communicating path, said discharge counter electrode being disposed between said pointed discharge electrode and said second chamber in such a manner that said penetration hole faces the end of said pointed discharge electrode and forms the inlet for light passing into said communicating path from said first chamber;
   an electrical power source connected to said pointed discharge electrode and said discharge counter electrode to establish an electrical discharge therebetween;
   means for introducing a discharge gas into said first chamber to effect ionization thereof by said electrical discharge which will effect the generation of light in said first chamber;
   means for introducing a sample gas into said second chamber to be photoionized by the light from said first chamber;
   means for exhausting the photoionized sample gas from said second chamber; and
   means including a collector electrode and a collector counter electrode disposed in said second chamber for measuring the ionization current of said sample gas.

2. A gas ionization detector according to claim 1, in which the wall of said communicating path is formed by an electric insulator.

3. A gas ionization detector according to claim 1, in which said discharge counter electrode is disposed in such a manner that any part of the periphery of said penetration hole is substantially at an equal distance from the tip of said pointed discharge electrode.

4. A gas ionization detector according to claim 1, in which the spatial cross-section of said communicating path is circular and the periphery of said discharge counter electrode surrounding said penetration hole is tapered toward the center of said hole.

5. A gas ionization detector according to claim 4, in which said discharge counter electrode is a planar member.

6. A gas ionization detector according to claim 1, in which said collector electrode is circular cylindrical in form and is disposed so that the sample gas is made to pass through said electrode.

7. A gas ionization detector according to claim 1, including means to direct the flow of said sample gas in said second chamber perpendicular to the direction of radiation of the light passing through said communicating path.

8. A gas ionization detector according to claim 1, including means to guide the flow of said sample gas along the direction of radiation of the light from said first chamber to said second chamber.

9. A gas ionization detector according to claim 1, in which said collector electrode and said collector counter electrode are disposed perpendicular to the direction of the flow of said sample gas.

10. A gas ionization detector according to claim 1, in which said discharge gas introduced into said first chamber is exhausted through said second chamber.

11. A gas ionization detector comprising:
a first chamber having a wall formed of an electrical insulating material;
a second chamber having a wall formed of an electrical insulating material;
means forming a communicating path between said first and second chambers to guide light from said first chamber into said second chamber;
a pointed discharge electrode placed in said first chamber and directed toward said communicating path;
a discharge counter electrode having a penetration hole with a size smaller than the spatial cross-section of said communicating path, said discharge counter electrode being disposed between said pointed discharge electrode and said second chamber in such a manner that said penetration hole is the inlet for light passing into and through said communicating path from said first chamber;
means covering the outer surface of the wall of said electrically insulating second chamber to provide an electric shield therefor;
an electrical power source connected to said pointed discharge electrode and said discharge counter electrode to establish an electrical discharge therebetween;
means for introducing a discharge gas into said first chamber to effect ionization thereof by said electrical discharge which will effect the generation of light in said first chamber;
means for introducing a sample gas into said second chamber to be photoionized by the light from said first chamber;
means for exhausting the photoionized sample gas from said second chamber; and
means including a collector electrode and a collector counter electrode disposed in said second chamber for measuring the ionization current of said sample gas.

12. A gas ionization detector according to claim 11, in which said means electrically shielding said second chamber is electrically connected to said collector counter electrode.

13. A gas ionization detector according to claim 12, in which said means electrically shielding said second chamber is formed in one united body with said collector counter electrode.

14. A gas ionization detector according to claim 11, in which the outer surface of the wall of said first chamber is covered with a metal member to provide an electric shield therefor.

15. A gas ionization detector according to claim 14, in which said member electrically shielding said first chamber is connected electrically to said discharge counter electrode.

16. A detector for gases comprising:
(a) a first chamber whose wall is made of an electric insulator;
(b) a second chamber into which a sample gas is introduced;
(c) a cylindrical communicating path by which said first and second chambers communicate, a wall forming said communicating path being made of an electric insulator;
(d) a counter discharge electrode in the form of a plate whose plane is put in substantially perpendicular to the axis of said communicating path, said counter discharge electrode having a penetration hole whose center axis is substantially coaxial to the center axis of said communicating path and whose diameter is less than that of said communicating path, an annular surface forming said penetration hole having a circular edge which is exposed to said first chamber;
(e) a pointed discharge electrode which is disposed in said first chamber so as to point the pointed end thereof at the center of said penetration hole;
(f) means for causing an electric discharge radiating light only between said pointed discharge electrode and said counter discharge electrode;
(g) means for introducing a discharge gas into said first chamber;
(h) means for exhausting gas which has passed through said second chamber;
(i) a collector electrode which is disposed in said second chamber;
(j) a counter collector electrode which is disposed in said second chamber, said counter collector electrode forming a part of a wall of said second chamber; and
(k) output signal display means connected with said collector electrode.

17. A detector for gases according to claim 16, wherein said pointed discharge electrode is located so that the distance between any point on said circular edge of said counter discharge electrode and said pointed end of said pointed discharge electrode is constant.

18. A detector for gases according to claim 16, wherein a direction of the flow of the sample gas in said second chamber is substantially perpendicular to the light radiating direction passing through said communicating path.

19. A detector for gases according to claim 16, wherein said discharge gas introduced into said first chamber is exhausted through said second chamber.

20. A detector for gases comprising:
(a) a first chamber whose wall is made of an electric insulator;
(b) a second chamber into which a sample gas is introduced;

(c) a cylindrical communicating path by which said first and second chambers communicate, a wall forming said communicating path being made of an electric insulator;

(d) a counter discharge electrode in the form of a plate whose plane is put in substantially perpendicular to the axis of said communicating path, and said counter discharge electrode having a penetration hole whose center axis is substantially coaxial to the center axis of said communicating path and whose diameter is less than that of said communicating path, an annular surface forming said penetration hole having a circular edge which is exposed to said first chamber;

(e) a pointed discharge electrode which is disposed in said first chamber so as to point the pointed end thereof at the center of said penetration hole;

(f) means for causing an electric discharge radiating light only between said point discharge electrode and said counter discharge electrode;

(g) means for introducing a discharge gas into said first chamber;

(h) means for exhausting gas which has passed through said second chamber;

(i) a cylindrical collector electrode and a cylindrical counter collector electrode which are disposed in said second chamber, said collector electrode and said counter collector electrode forming a part of a wall of said second chamber; and (j) output signal display means connected with said collector electrode.

21. A detector for gases according to claim 20, wherein said collector electrode and said counter collector electrode are disposed coaxially, said counter collector electrode being disposed on the upstream side of the sample gas flow, and said collector electrode being disposed on the downstream side of the sample gas flow.

22. A detector for gases according to claim 21, the diameters of said collector electrode and said counter collector electrode are larger than that of said communicating path.

23. A detector for gases according to claim 20, wherein said penetration hole, said communicating path, said collector electrode and said counter collector electrode are disposed coaxially.

24. A detector for gases comprising:

(a) a first chamber whose wall is made of an electric insulator;

(b) a second chamber into which a sample gas is introduced, a wall forming said second chamber being made of an electric insulator;

(c) a cylindrical communicating path by which said first and second chambers communicate, a wall forming said communicating path being made of an electric insulator;

(d) a counter discharge electrode in the form of a plate whose plane is put in substantially perpendicular to the axis of said communicating path, said counter discharge electrode having a penetration hole whose center axis is substantially coaxial to the center axis of said communicating path and whose diameter is less than that of said communicating path, an annular surface forming said penetration hole having a circular edge which is exposed to said first chamber;

(e) a pointed discharge electrode which is disposed in said first chamber so as to point the pointed end thereof at the center of said penetration hole;

(f) means for causing an electric discharge radiating light only between said pointed discharge electrode and said counter discharge electrode;

(g) means for introducing a discharge gas into said first chamber;

(h) means for exhausting gas which has passed through said second chamber;

(i) a collector electrode which is disposed in said second chamber;

(j) a counter collector electrode which is disposed in said second chamber, said counter collector electrode forming a part of a wall of said second chamber;

(k) a metal member with which said insulative wall of said second chamber is covered on the outside thereof so as to electrically shield said second chamber; and (l) output signal display means connected with said collector electrode.

25. A detector for gases according to claim 24, wherein said wall of said first chamber is covered with a metal member on the outside thereof.

26. A detector for gases according to claim 24, wherein said metal member electrically shielding said second chamber is electrically connected with said counter collector electrode.

27. A detector for gases according to claim 26, wherein said metal member electrically shielding said second chamber and said counter collector electrode are united in a body.

* * * * *